United States Patent [19]

Evans et al.

[11] 4,271,832
[45] Jun. 9, 1981

[54] POST-FRACTURE STABILITY OF LIMBS

[75] Inventors: Mervyn Evans, Kidlington; John D. Harris, Abingdon, both of England

[73] Assignee: National Research Development Corporation, London, England

[21] Appl. No.: 59,201

[22] Filed: Jul. 20, 1979

[30] Foreign Application Priority Data

Jul. 20, 1978 [GB] United Kingdom ............... 30575/78

[51] Int. Cl.³ .............................................. A61F 5/04
[52] U.S. Cl. .................................................. 128/92 A
[58] Field of Search ............. 128/92 A, 92 R, 92 BC, 128/92 BA, 92 E, 92 EA, 92 EB

[56] References Cited
U.S. PATENT DOCUMENTS

| 2,346,346 | 4/1944 | Anderson | 128/92 A |
|---|---|---|---|
| 2,391,537 | 12/1945 | Anderson | 128/92 A |
| 2,697,433 | 12/1954 | Zehnder | 128/92 EB |
| 3,961,854 | 6/1976 | Jaquet | 128/92 A |
| 3,975,032 | 8/1976 | Bent et al. | 128/92 E |
| 4,127,119 | 11/1978 | Kronner | 128/92 A |

Primary Examiner—Robert W. Michell
Assistant Examiner—C. W. Shedd
Attorney, Agent, or Firm—Cushman, Darby & Cushman

[57] ABSTRACT

A post-fracture bone immobilization splint for unilateral fixation comprises a rigid bar on which are slidably mounted at least four pin clamps. Each pin clamp is fixable to the bar and is provided with a pin to engage a part of the fractured bone. The pin is supported in two holes diametrically located in a hollow cylindrical portion of the pin clamp, the diameter of the holes being larger than the pin diameter such that the pin can be adjusted slidingly as well as azimuthally within a limited range of zenith angles. The annular gap surrounding the pin is sealed by surrounding moveable washers which are spaced apart within cylindrical portion by a plastic tube through which the pin passes. The remainder of the hollow portion is filled with small ball bearings that are compressible by a threaded plug. The pin is positioned as desired and the threaded plug is then rotated to compress the ball bearings which deform the plastic tube and thereby grip the pin. Under greater compressive force, the ball bearings will penetrate the plastic tube and deformably engage the pin.

6 Claims, 6 Drawing Figures

POST-FRACTURE STABILITY OF LIMBS

The invention relates to the holding of fractured limb bones and in particular to devices for externally positioning and holding bone ends in their correct relationship while the fracture mends.

The method of dealing with broken limb bones involving the use of plaster casts has required long rehabilitation. Alternatively, internal fixation of broken bones using plates to clamp together the parts of a broken bone has allowed the restoration of the normal anatomy and early joint movement, thereby leading to a faster rehabilitation and a fuller eventual recovery. However a significant incidence of grave complications has resulted from internal fixation.

To overcome these difficulties various systems of external fixation have been tried. These systems have been used in general in the following situations:

(a) For severe open fractures these systems can stabilise the fracture so that the soft issue can be treated effectively.

(b) For fractures where there is difficulty in controlling the position but where there is unhealthy skin making internal fixation dangerous.

(c) For un-united fractures with unhealthy skin where bone graft is needed with simultaneous fixation of the fragments.

(d) For multiple limb fractures with difficulty of control of the position of the combination of fractures.

(e) For infected non-union of fractures.

External fixation devices fall into two categories: bilateral fixation requiring pins to pass right through the limb in order to obtain sound bone fragment fixation and unilateral fixation employing pins which are screwed into the bone fragments.

The prior art external fixation arrangements have generally suffered one or more of the disadvantages of being bulky, being complex and thus expensive, having little scope for adjustment and having inadequate strength.

The object of the invention is to provide a post-fracture bone immobilization splint combining strength, lightness and lack of bulk with ease of adjustment to allow the patient to use the broken limb as quickly as possible.

The invention provides a post-fracture bone immobilization splint comprising a rigid immobilizer bar having slidably mounted thereon at least four pin clamps each pin clamp being fixable to the bar and provided with a pin to engage a part of the fractured bone and each pin being lockably mounted in a respective pin clamp such that it can be adjusted slidably and in azimuth within a limited range of zenith angles with respect to the median axis of the pin. Preferably each pin has a self-tapping screw thread which can be screwed into the bone. In a simple break two pins are screwed into each part of the broken bone, but more can be used if necessary. The pins are then clamped to the bar, the arrangement being such as to allow a considerable degree of universal adjustment so that after the screws are positioned in the bone the orientation of the bone parts can be subsequently revised. Preferably standard Schantz screws are used.

The rigid bar is preferably rectangular in cross-section whereby rotation of the pin clamps about the axis of the bar is prevented. For lightness and strength the bar can be made of square section tube of stainless or chromium plated steel. Preferably each pin clamp comprises a first portion having a rectangular channel therethrough for engaging the bar and means to lock the pin clamp to the bar. Each pin clamp has a second portion provided with the means to lock the pin. The second portion comprises a hollow cylindrical section integrally connected at one end to the first portion and provided therethrough with a hole transversely of and intersecting cylinder axis, the pin being releasably clamped therein. Preferably the diameter of the hole through the cylindrical section is larger than the diameter of the pin such that the pin can slide therethrough and be adjustable in azimuth and in zenith with respect to the median pin axis. The limit of the zenith angular adjustment is determined by the ratio of the hole diameter to the pin diameter. Advantageously two washers are provided inside the cylindrical section each washer having an external diameter greater than the diameter of the hole and an internal diameter such that the washer is a sliding fit on the pin, spacer means being provided to hold each washer adjacent to a respective hole in the wall of the cylindrical section of the clamp whereby the pin passes through each washer. Preferably the spacer means comprises a plastics tube through which the pin also passes. The means to clamp the pin in position may comprise a plurality of ball bearings which are contained within the hollow cylindrical section of the pin clamp and are compressed so as to securely grip the pin in a predetermined position. Preferably the plastics tube is thin-walled and the material soft such that on compression some of the balls puncture the plastics and make indentations in the pin so as to securely grip the pin. The means to compress the ball bearings preferably comprises a plug which can be screwed into the cylindrical section of the clamp.

Independent control of the two parts of a simply fractured bone is desirable during treatment, after the initial application of the bone immobilization splint to the fracture. In addition post-operative control is possible as is required for example in leg lengthening where the two parts of a bone, fractured during an operation, are gradually separated in small discrete steps over a period of time. Advantageously the adjustment is made by means of a detachable extension/compression device so that the patient is not encumbered by an unnecessarily bulky or heavy bone immobilization splint. Preferably the adjustment device comprises two or more adjustment clamps each securable to a pin clamp and slidably mounted on an adjustment bar and lockable in a preselected position along the adjustment bar and an adjustor connectable to the bone immobilizer bar and attached to the adjustment bar such that on releasing the pin clamps from the bone stabiliser bar the adjustor may be operated to move the two or more pin clamps along the bone immobilizer bar. The adjustment bar may be provided with a screw thread which engages a captive nut on the adjustor.

The invention will be described by way of example only with reference to the accompanying figures of which:

Figure 1:
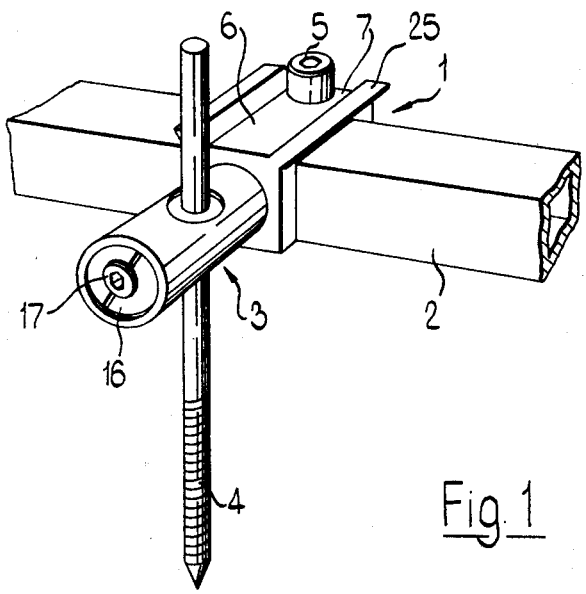
FIG. 1 is a perspective view of a section of the bone immobilization splint.
Figure 2:
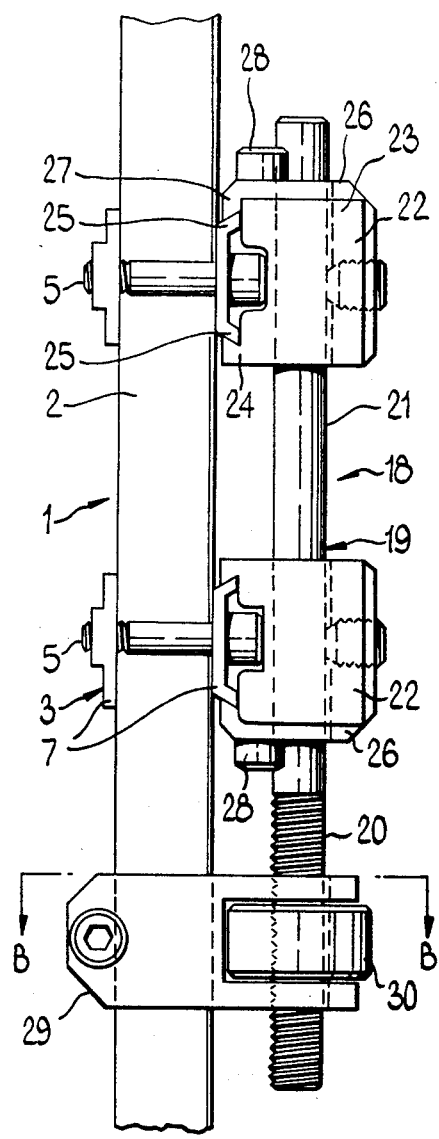
FIG. 2 is a side elevation view of the bone immobilization splint together with a detachable adjustment device.
Figure 3:
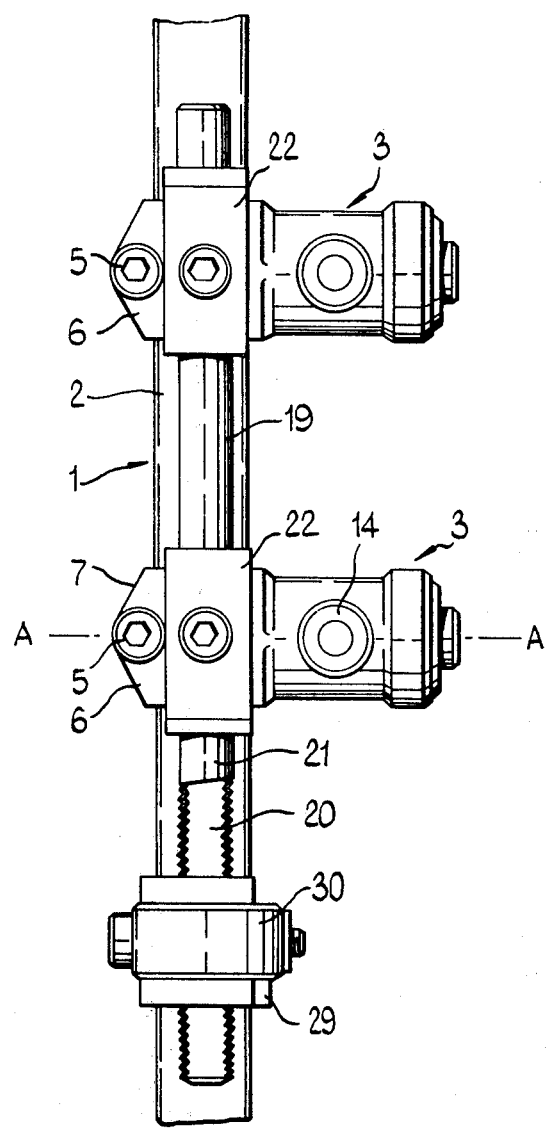
FIG. 3 is a plan view of the apparatus of FIG. 2.

The bone immobilization splint 1 shown in FIGS. 1 to 3 comprises a rigid square sectioned immobilizer bar 2 of chrome or stainless steel tube which is positioned to be parallel and close to the fractured limb. Attached to this bar are a number of pin clamps 3. Each pin clamp 3 holds a 6 mm pin or extended self-tapping bone screw 4, or Schantz screw, which is first screwed into the fractured bone and then rigidly held in the pin clamp. Typically two pins 4 are fixed above the fracture and two pins fixed below, but more can be used if necessary. In addition small sound bone fragments can be fixed by further pins when required.

The pin clamps 3 are designed such that they may be locked in any position along the bar 2 by means of bolts 5. Each pin clamp 3 has a first portion 6 having a rectangular channel therethrough so as to form a U shaped channel for insertion of the bar 2. The two limbs 7 of the channel extend beyond the bar 2 such that bolts 5 can be inserted therethrough to lock the pin clamp 3 to the bar.

Figure 4:
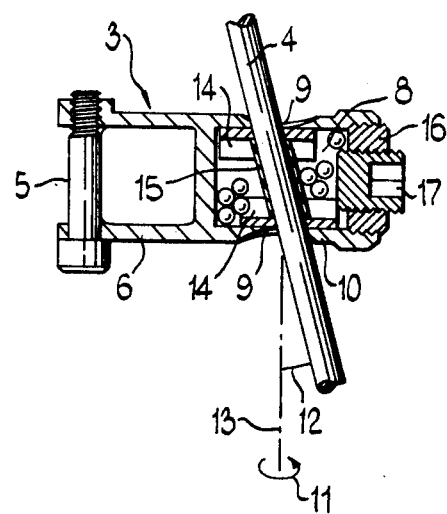
FIG. 4 is a cross sectional view of a pin clamp taken along the line A—A of FIG. 3.

FIG. 4 shows a cross-section through the pin clamp 3. A second portion 8 of the pin clamp 3 is circular in cross section and has circular holes 9 formed in diametrically opposed positions in the circular wall 10. The diameter of the holes 9 is chosen to be greater than the diameter of the pin 4 so that an insertion through the holes 9 the pin 4 can be adjusted to any azimuth angle 11 within a limited range of zenith angles 12 defined about the axis 13 through the holes 9. Typically the maximum zenith angle may be about 12°. Arranged inside the cylindrical portion 8 are two part-cylindrical washers 14 which are a sliding fit on the pin 4 and conform with the inside surface of the wall 10 of portion 8 and are of such size as to allow movement of the pin 4 through the range of zenith angles 12 while sealing the holes 9. The washers 14 are maintained in contact with the wall 10 by means of a thin-walled cylindrical plastics sleeve 15 which extends between the washers and is a sliding fit over the pin 4. A thread is provided at the end of the cylindrical wall 10 such that a plug 16 can be screwed into the cylindrical portion 8. A number of ⅛ inch ball bearings are inserted into the space inside portion 8 surrounding the pin 4 in the plastics sleeve 15. On tightening the plug 16 the ball bearings press on the pin 4 so as to hold it in a predetermined position. A soft plastics material such as PVC is chosen for the sleeve 15 such that some ball bearings are able to puncture the sleeve and make slight indentations in the pin 4 thereby providing a firm hold on the pin 4. The plastics material must also be capable of withstanding a sterilisation temperature in excess of 100° C. The plug 16 has a smaller screwed plug 17 provided in a threaded hole therethrough whereby the final locking of the pin 4 can be done by screwing the smaller plug 17.

In practice when setting a simple fracture a drilling jig is used which comprises the bar 2 and four lockable drill guides similar to the clamps 3. The two outer guides are first used to drill holes through the two parts of the fractured bone and finally the two inner holes are drilled. Since the bone might not be straight (when unbroken) it may be desirable to drill the two central holes at an angle with respect to the outer two. The drill guides are provided with a fixed bush for drilling perpendicularly to the bar 2 or with a rotatable bush to allow laterally angled drilling up to a maximum angle which is within the limit of the angular adjustment of the pins 4 within the pin clamps 3. By this means the screwed pins 4 can be inserted to provide the strongest possible grip. A drill chuck is then connected to each of the pins 4 in turn and the pins 4 are screwed into and just through the bone such that threaded portions of the pins 4 engage the outer bone cortex.

Figure 5:
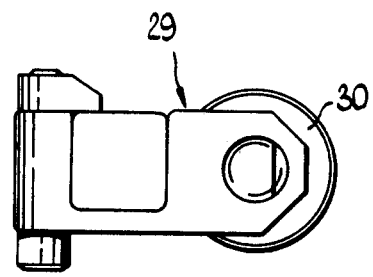
FIG. 5 is a side elevation of an adjustor in the direction B—B shown in FIG. 2.

FIGS. 2 and 3 show a detachable extension/compression device 18 by means of which the two bone parts, once supported by the bone immobilization splint 1 can be linearly brought together or separated to obtain the correct limb length. The device 18 comprises a cylindrical bar 19 having an end threaded portion 20 and a remaining portion having one flattened surface 21. The bar 19 is placed parallel and close to the immobilizer bar 2 and two adjustment clamps 22 are fixed to the bar 19 by means of screws which engage the flattened surface 21 of the bar 19 and one to each of the stabiliser pin clamps 3 supporting one part of the fractured bone. The adjustment clamp 22 has a main body portion 23 provided with a recessed groove 24 adapted to fit over a projection 25 provided therefor on the portion 6 of the pin clamp 3. The adjustment clamp 22 also includes a plate 26 having a raised edge 27 for engaging a second projection 25 on the pin clamp 3. By bringing the two portions of the adjustment clamp 22 together by means of screw 28 the clamp 22 can be locked to the pin clamp 3. FIGS. 2, 3 and 5 show an adjustor 29 which is locked to the immobilizer bar 2. The adjustor includes a captive nut 30 which engages the threaded portion 20 of the bar 19. Compression or extension of the limb is achieved by first locking on the adjustment device 18, loosening the bolts 5 locking the two pin clamps 3 to the stabiliser bar 2, and then moving one bone part by rotation of the nut 30. The captive adjustment nut 30 is provided with circumferential numbering such that adjustment of the number by one integer corresponds to the periodic adjustment in compression or extension which is required. Typically this might be about 0.5 mm per day.

Figure 6:
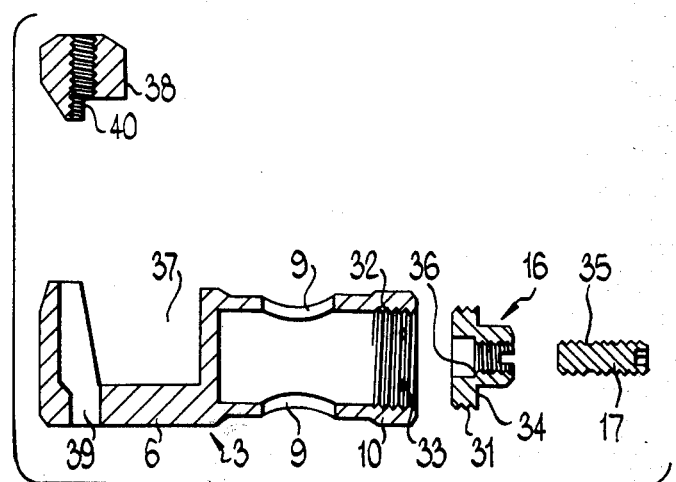
FIG. 6 is an exploded sectional view of an alternative pin clamp.

In an alternative arrangement of the pin clamp 3 as shown in FIG. 6 the plug 16 is provided with a relatively short threaded portion 31 to engage a relatively longer complementary threaded portion 32 on the inside of the cylindrical wall 10 of the pin clamp 3. Four circumferential holes 33 are located near the axially outer extremity of the cylindrical wall 10 such that a generally U-shaped spring clip (not shown) can be inserted therethrough. The U-shaped spring dip is inserted through the holes 33 to retain the plug 16 by engagement with the circumferential step 34 on the plug 16. The smaller screwed plug 17 is provided with a groove 35 for receiving a circlip (not shown) to engage the recessed step 36 in the plug 16 and thereby retain the smaller plug 17. By this means the pin 4 can be clamped or slackened by adjustment of the coarse adjustment plug 16 and the smaller fine adjustment plug 17 while preventing a loss of ball bearings from within the pin clamp 3. The first pin clamp portion 6 is provided with a channel 37 for receiving the square sectioned bar 2. A threaded wedge 38 is engaged by a bolt passing through the hole 39 in the pin clamp 3. The recess 40 in the wedge 38 engages one corner of the bar 2 such that on tightening the bolt the bar becomed wedged into the channel 37. The pin clamp shown in FIG. 6 has several advantages compared to that shown in FIG. 4:

(a) A firmer fixing is obtained without the need for tight tolerances;

(b) The pin clamp 3 can be electrically insulated from the bar 2 so that electrical stimulation of the bone fragment via the pin 4 can be performed; and (c) Easier assembly of the pin clamp 3 to the bar is possible since the pin clamp is applied in a direction substantially colinear with the pin axis.

With this arrangement a simpler method of attachment of the adjustment clamps 22 of the extension/compression device has been used. The first portion 6 of the pin clamp 3 is provided with a threaded hole for attachment to the adjustment clamp 22 by means of a bolt passing therethrough. By this means the adjustment clamps can be attached to the appropriate pin clamps 3 without the necessity for a sliding engagement of the pin clamp projections 25 as in the arrangement shown in FIG. 2. The adjuster 29 is also modified so that it can be attached to the bar 2 in like manner to the pin clamp 3 shown in FIG. 6.

The limb bone immobilization splint is primarily for use in leg fractures where most of the fractures are to the tibia. By inserting pins from one side of the leg only, minimum disruption of the leg muscles and thus the maximum flexibility of the leg joints can be achieved. Since the pin clamps 3 can accommodate various angular dispositions of the pins 4, the pins can be drilled optimally into the parts of the fractured bone and a lesser accuracy is required in drilling and inserting the screw pins. By a suitable choice of washers used in the pin clamps various sizes of pin can be used; for example a smaller pin could be used for a child's limb. The pin clamps also are able to take up a small amount of lateral inaccuracy in positioning of the pins. The holes 9 could be made ovular so as to accommodate a greater lateral tolerance transverse to the immobilizer bar.

Other modifications to the embodiment described while falling within the scope of the invention will be apparent to those skilled in the art. It is envisaged for example that the bone immobilization splint could be used to support the two bones of a joint in order to immobilise the joint or by the use of modified Schantz screws the invention could be adapted for bilateral fixation. The median axis of the pin 4 need not be perpendicular to the bar 2. In special cases where greater stability is required the median axis of the pin could be chosen to be for example 20° from the perpendicular with a range of angular adjustment of ±10°.

I claim:

1. A splint for immobilizing a fractured bone comprising:
    a rigid bar;
    at least four pin clamps slidably mounted on said bar and fixable thereto;
    at least four pins, each corresponding to a different one of said at least four pin clamps, each pin being capable of being lockably mounted in a different corresponding one of said at least four pin clamps and capable of engaging a part of the fractured bone;
    each of said at least four pin clamps including a hollowing cylindrical portion having a cylindrical wall formed with two diametrically opposed openings, said two openings having diameters greater than the diameter of said corresponding pin, said corresponding pin extending through said two openings when lockably mounted;
    each of said at least four pin clamps being structurally identical and further including:
    two washers slidably fit on said corresponding pin inside said cylinder, each washer being positioned adjacent to and having an external diameter greater than the diameter of said openings in said cylinder;
    a plastic tubular spacer slidably fit on said corresponding pin between said two washers so as to hold each of said two washers against a corresponding one of said two openings;
    a plurality of ball bearings contained in the space remaining in said cylinder when said corresponding pin, said two washers and said plastic spacer are disposed in said cylinder; and
    means for applying pressure to said ball bearings to clamp said corresponding pin;
    said corresponding pin, when in position to be clamped by said plurality of ball bearings, extends through said two openings in said cylinder, through said two washers and through said plastic spacer; said two washers being moveable by said corresponding pin when said means for applying pressure is not applied, to allow limited universal angular adjustment of said corresponding pin relative to said clamp; said two washers retain said plurality of ball bearings in said cylinder.

2. A splint according to claim 1 wherein the bar is rectangular in cross-section.

3. A splint according to claim 2 wherein the bar is a square section tube.

4. A splint according to claim 1 wherein the plastics tube is thin walled and is such that on compression of the ball bearings, some of the balls puncture the plastics and make indentations in the pin so as to securely grip the pin.

5. A splint according to claim 1 or claim 4 further comprising an adjustment bar; a detachable adjustment device comprising at least two adjustment clamps each securable to different ones of said pin clamps and lockably mounted on said adjustment bar, and an adjustor connectable to said rigid bar and attached to said adjustment bar such that on releasing said different pin clamps from said rigid bar, said adjustor can be operated to move said released pin clamps along said rigid bar.

6. A splint according to claim 5 wherein the adjustment bar has a screw-threaded portion which engages a captive nut on the adjustor.

* * * * *